United States Patent
Prescott et al.

(10) Patent No.: US 6,487,921 B1
(45) Date of Patent: Dec. 3, 2002

(54) FLUIDIZATION SEGREGATION TESTER

(75) Inventors: James K. Prescott, Shrewsbury, MA (US); Scott A. Clement, San Luis Obispo, CA (US); John W. Carson, Chelmsford, MA (US)

(73) Assignee: Jenike & Johanson, Inc., Westford, MA (US)

( * ) Notice: Subject to any disclaimer, the term of this patent is extended or adjusted under 35 U.S.C. 154(b) by 98 days.

(21) Appl. No.: 09/697,217

(22) Filed: Oct. 26, 2000

(51) Int. Cl.[7] .................................................. G01N 1/00
(52) U.S. Cl. ................................... 73/863.21; 73/865.5
(58) Field of Search ........................... 73/863.56, 865.5, 73/863.21, 863.71, 863.72, 863.73

(56) References Cited

U.S. PATENT DOCUMENTS

| | | | | |
|---|---|---|---|---|
| 3,690,179 A | * | 9/1972 | Olson | 73/863.56 |
| 3,714,833 A | * | 2/1973 | Newman | 73/865.6 |
| 4,640,140 A | * | 2/1987 | Burghoffer et al. | 73/863.22 |
| 4,718,288 A | * | 1/1988 | Leschonski | 73/863 |
| 5,583,304 A | | 12/1996 | Kalidindi | 73/863.56 |

* cited by examiner

Primary Examiner—Hezron Williams
Assistant Examiner—Nashmiya Fayyaz
(74) Attorney, Agent, or Firm—Lahive & Cockfield, LLP

(57) ABSTRACT

Apparatus providing samples for evaluating the sensitivity of bulk particulate solids to segregation when permeated by a gas. A plurality of stacked discs are rotatably mounted on a vertical shaft.

Each disc has a bore, the bores being alignable to form a columnar sample chamber. A gas is introduced under pressure at the bottom of the chamber to fluidize the solids, inducing segregation. Apertures in the discs are adapted to support sample jars. The discs are independently and sequentially rotatable to cause the portion of the segregated sample within each bore to be separately deposited in a sample jar.

8 Claims, 6 Drawing Sheets

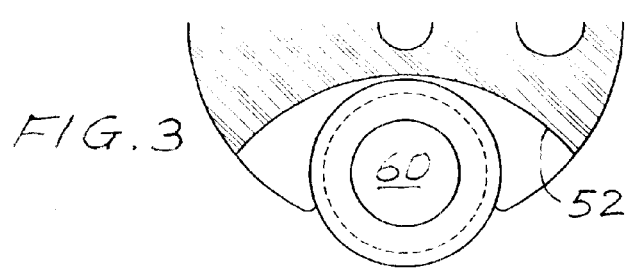
FIG. 3
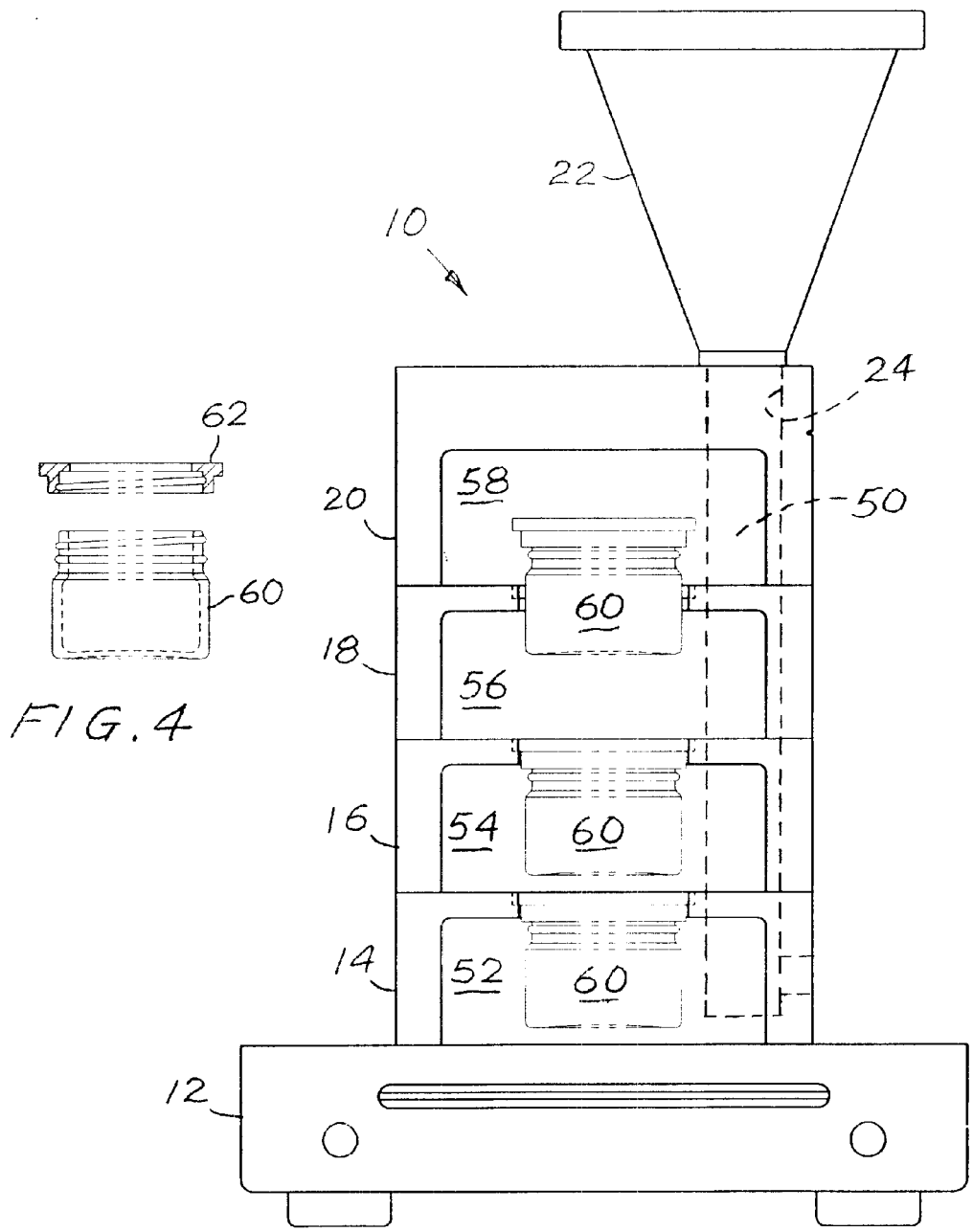
FIG. 4
FIG. 2

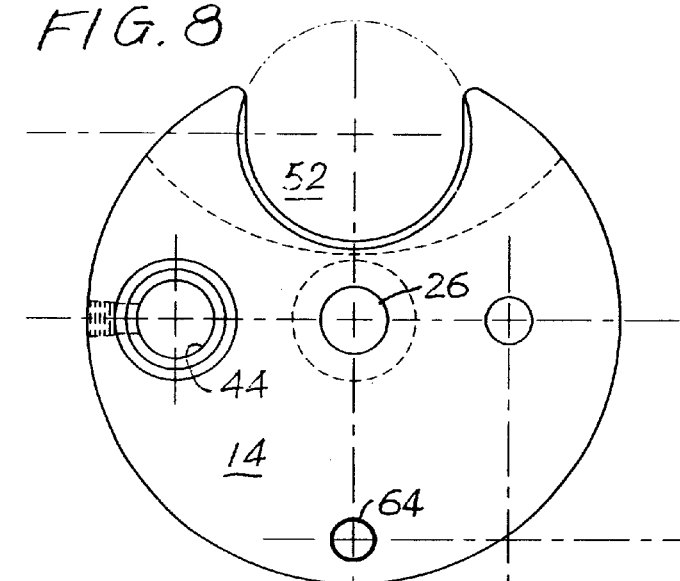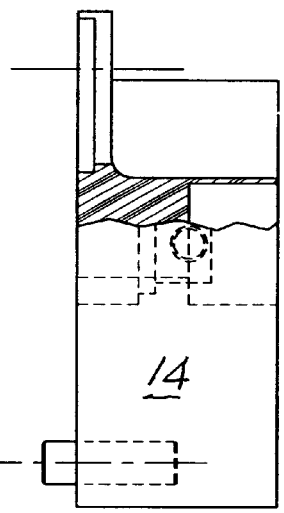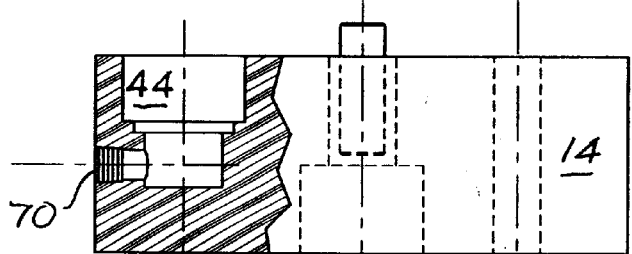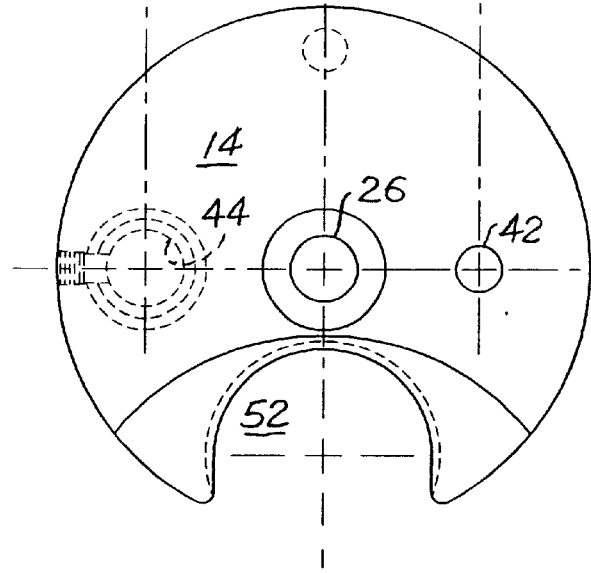

FLUIDIZATION SEGREGATION TESTER

BACKGROUND OF THE INVENTION

This invention relates generally to methods and apparatus for evaluating the tendency of sample bulk particulate solids to segregate by fluidization or exposure to permeation by gases. More particularly, it relates to apparatus for controlled fluidization of a vertical column of the solids by a gas such as air and subsequent collection of samples from separate segments of the column. The samples are suitable for conventional evaluation and comparison by screening, assays or other measurements to quantify the potential segregation by fluidization effects or gas entrainment.

Bulk solids generally comprise particles of different sizes. It is commonly desirable to maintain a uniform concentration of each size throughout the body during industrial processing, storage and packaging. However, segregation of the particles by size frequently occurs during processing steps such as the filling or discharge of a bin, tumble blending, pneumatic conveying and other gas assisted bulk solid handling processes. As a result of segregation by fluidization, different regions within a body of the solids comprise different proportions of fine and coarse particles and uniformity of the mixture is lost.

Vertical segregation frequently occurs, resulting in horizontal layers comprising differing proportions of fine and coarse particles. Fine particles generally have a lower permeability for gas than coarse particles and therefore tend to retain the gas longer. Thus for example, on filling a hopper the coarse particles tend to become more concentrated in the lower layers while the fine particles become more fluidized and tend to become concentrated in the upper layers. Similar effects occur after tumble blending if the solids are susceptible to fluidization. These effects are particularly noticeable in materials that contain a significant concentration of particles below 100 microns in size. Fluidization segregation is also likely to occur when fine materials are pneumatically conveyed, filled or discharged at high rates, or if gas counterflow is employed.

A principal object of this invention is to provide a test method and apparatus for precisely controlled fluidization of a sample body of particulate solids, followed by the separate retrieval of portions of the sample from different vertical levels of the fluidized body.

A second object is to provide apparatus that facilitates the retrieval of the segregated samples without disturbing the state of the samples.

A third object is to provide test apparatus adapted for improved containment of the sample solids during the test procedure. This is particularly desirable for the testing of very fine powders.

A further object is to provide apparatus adapted for accurately repeatable fluidization of successive samples, permitting greater reliability and accuracy in comparing the results of repeated test procedures on samples from the same body of bulk solid or from differing bodies of solids.

BRIEF SUMMARY OF THE INVENTION

With the above and other objects hereinafter appearing in view, this invention provides apparatus for obtaining samples of bulk particulate solids from a columnar sample chamber containing fluidized particulate solids, for evaluating their sensitivity to segregation by fluidization. The apparatus includes a plurality of stacked discs rotatably mounted on a vertical shaft. The discs are provided with bores that are alignable to form a columnar sample chamber comprised of segments each to be separately collected. The discs are also provided with apertures for supporting sample jars, and the discs are independently and sequentially rotatable to cause the segment of the segregated sample solids within the bore of each disc to be separately deposited in a sample jar.

Means are provided to compress the discs during fluidization, thus minimizing leakage. When the discs are being rotated the compression force is reduced.

Other features, as hereinafter described, are employed to provide a compact apparatus in which the fluidization is precisely controlled for uniformity in repeated tests, thus increasing the reliability of evaluation procedures for comparing the results of separate samplings of the same or different solids.

DESCRIPTION OF THE DRAWINGS

FIG. 2 is a front elevation of the apparatus on a reduced scale.

FIG. 3 is a fragmentary plan view in section corresponding to FIG. 2.

FIG. 4 is an elevation showing a sample jar and its adapter.

FIG. 8 is a plan view of the bottom disc.

FIG. 9 is an elevation partly in section corresponding to FIG. 8.

FIG. 10 is a bottom view of the bottom disc.

FIG. 11 is a side elevation corresponding to FIG. 8.

DETAILED DESCRIPTION

Figure 1:
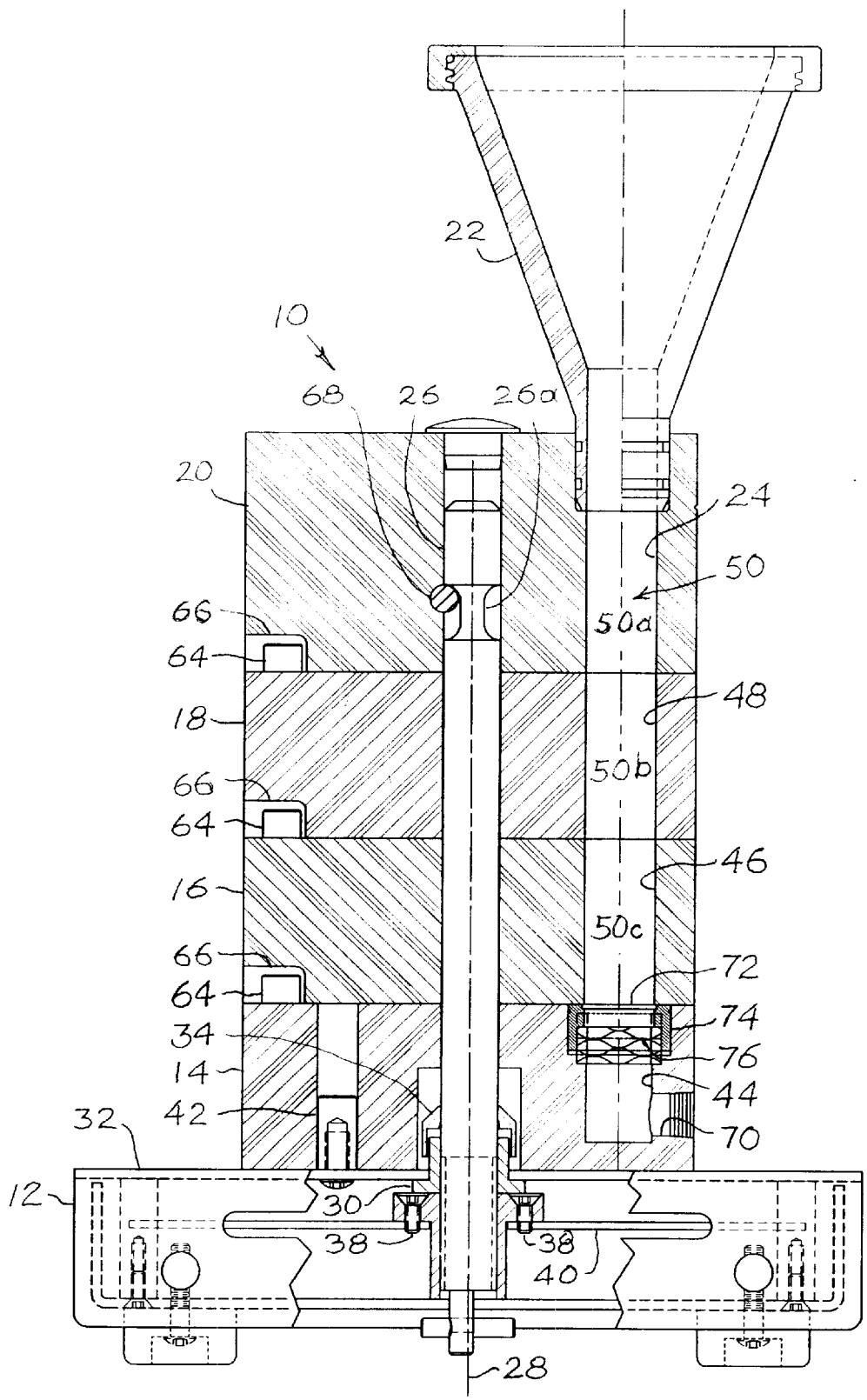
FIG. 1 is an elevation in section through the sample chamber of the presently preferred embodiment of the invention.

The preferred embodiment of the invention, shown generally at 10 in FIGS. 1 and 2, comprises a base 12 preferably constructed of metal, a bottom disc 14 shown in detail in FIGS. 8, 9, 10 and 11, intermediate discs 16 and 18 which are of similar construction as shown in detail for the disc 16 in FIGS. 12, 13, 14 and 15, and a top disc 20 shown in detail in FIGS. 16, 17, 18 and 19.

The tester 10 also includes a detachable funnel 22 insertable in a counterbored recess within a thru bore 24 in the disc 20. The sloping wall of the funnel is sufficiently steep to satisfy the conditions for recovery (flow) of any of the particulate solids to be tested by the apparatus.

Figure 5:
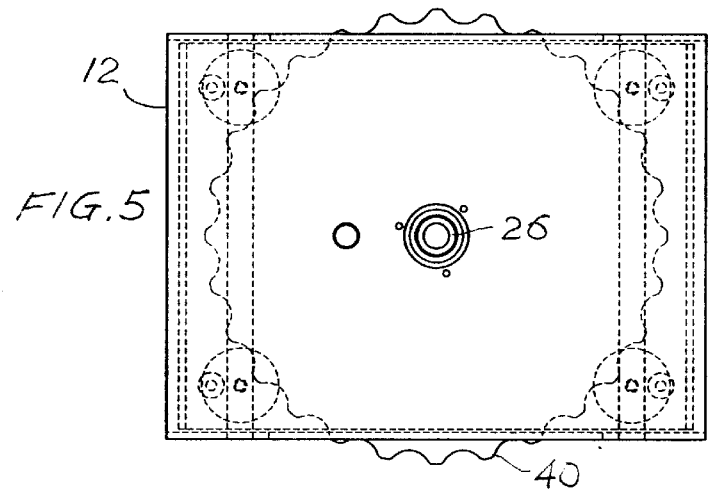
FIG. 5 is a plan view of the base of the apparatus.
Figure 6:
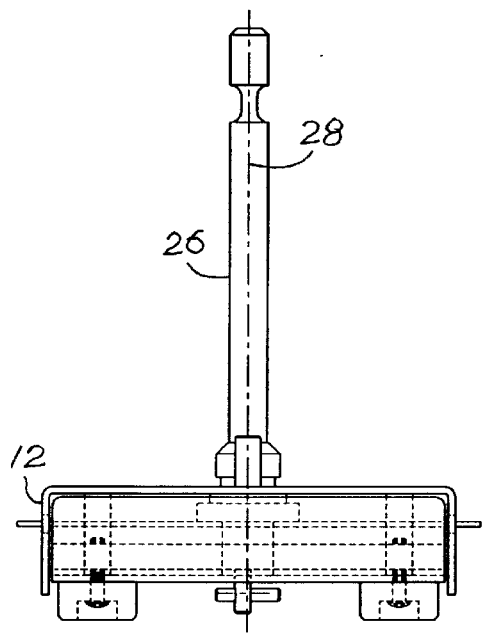
FIG. 6 is an elevation of the subassembly of the base and shaft of the apparatus.
Figure 7:
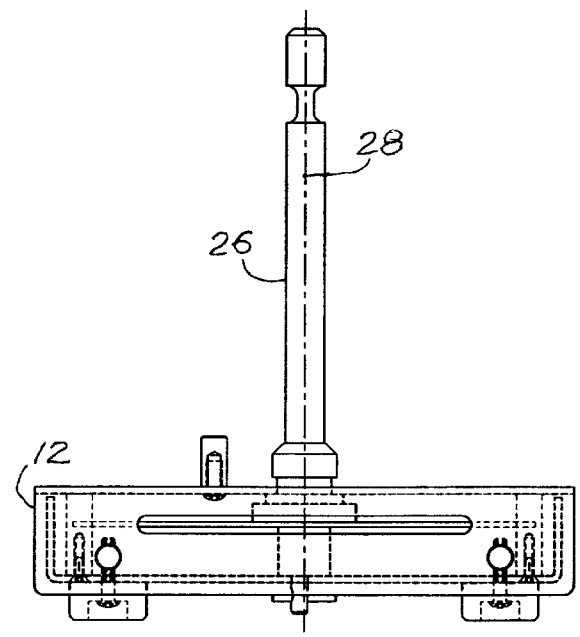
FIG. 7 is an elevation similar to FIG. 6 at right angles thereto.
Figure 12:
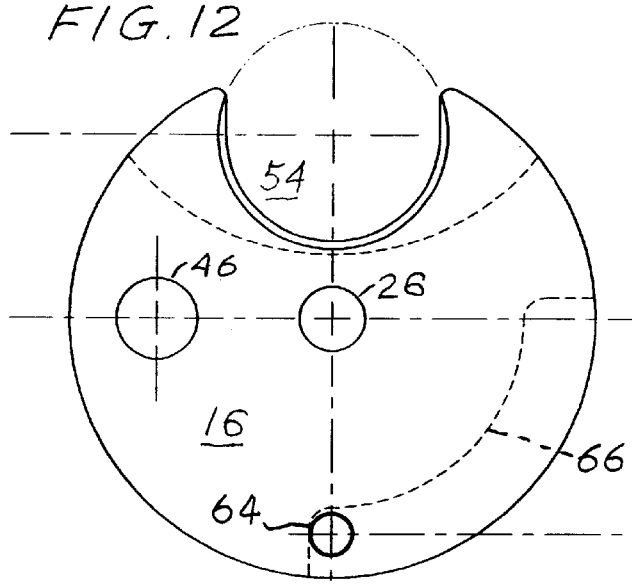
FIG. 12 is a plan view of an intermediate disc.
Figure 15:
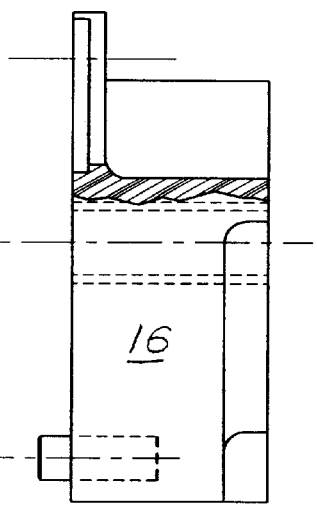
FIG. 15 is a side elevation corresponding to FIG. 12.
Figure 13:
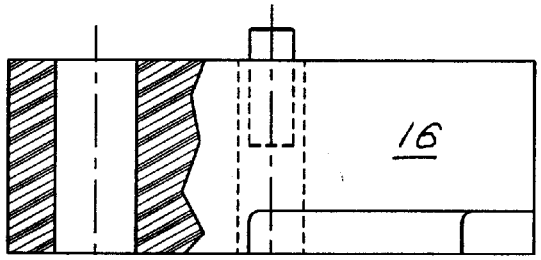
FIG. 13 is an elevation partly in section corresponding to FIG. 12.
Figure 14:
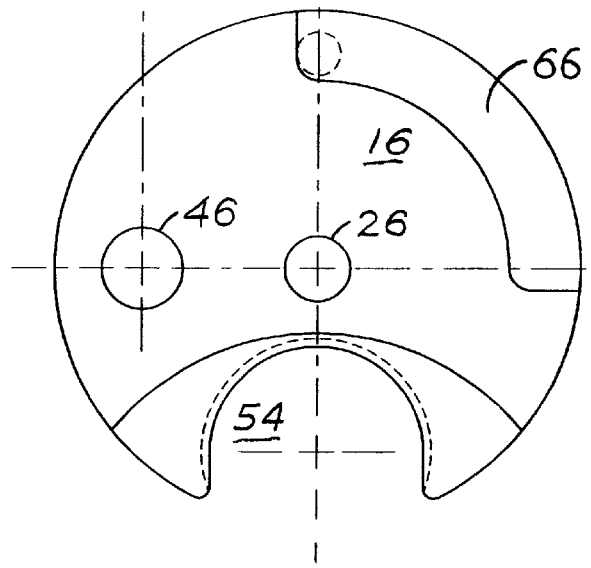
FIG. 14 is a bottom view of an intermediate disc.
Figure 16:
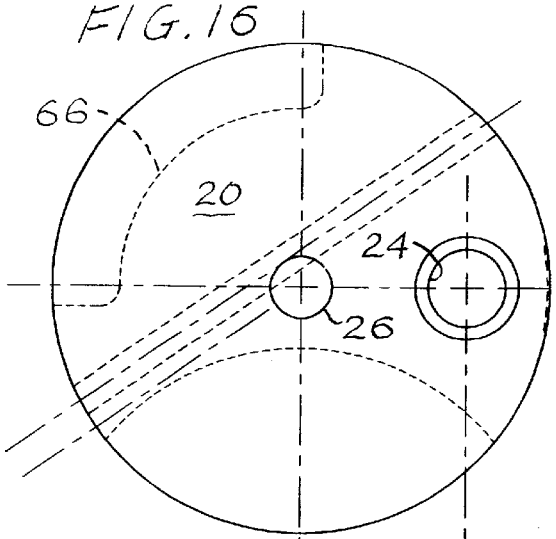
FIG. 16 is a plan view of the top disc.
Figure 19:
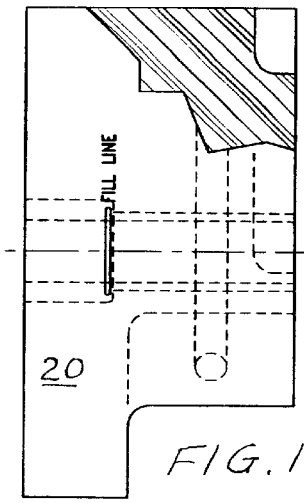
FIG. 19 is a side elevation partly in section corresponding to FIG. 16.
Figure 17:
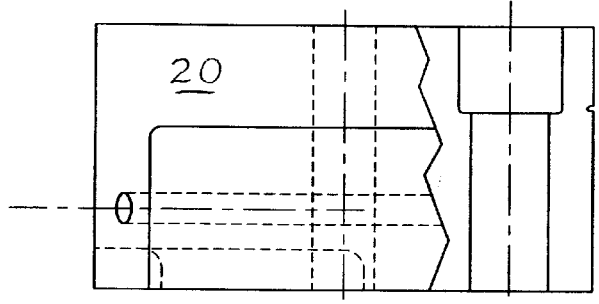
FIG. 17 is an elevation partly in section corresponding to FIG. 16.
Figure 18:
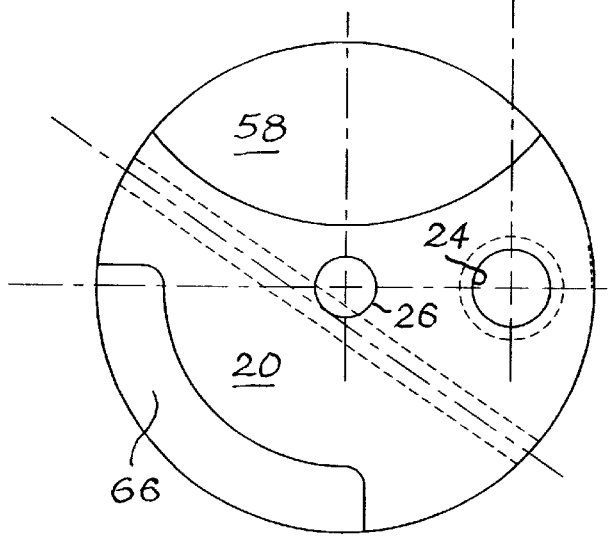
FIG. 18 is a bottom view of the top disc.

The base 12 supports a vertical shaft 26 on a fixed axis 28, and means are provided within the base for adjustable axial movement of the shaft. Details of the shaft support are shown in FIGS. 1, 5 and 7. The shaft 26 is slidably supported vertically and rotatably within a flanged sleeve 30 fixed to a cover plate 32 on the base. A dust cap 34, press fit on the shaft within a central recess in the disc 14, fits slidably over the sleeve 30. A flanged adjusting wheel hub 36 bears upwardly on the sleeve 30 and downwardly on the bottom of the base 12. The hub 36 is threaded on the shaft 26 and is secured by screws 38 to a thumb wheel 40. Thus rotation of the wheel 40 produces axial movement of the shaft 26.

The discs 14, 16, 18 and 20 are preferably formed of an acrylic plastic material, of cylindrical shape, bored axially and received over the shaft 26 in stacked formation. The intermediate discs 16 and 18 and the top disc 20 are rotatable on the shaft. The bottom disc 14 is prevented from rotation by a pin 42 screwed onto the cover plate 32 of the base and extending into a bore in the disc 14. Since the disc 14 is fixed in position relative to the base 12 in use, it may be made integral with the base if desired.

The discs 14, 16 and 18 are provided with bores 44, 46 and 48, respectively. Each of the discs 16, 18 and 20 is rotatable on the shaft to a position in which all of the bores 44, 46, 48 and 24 are axially aligned with the hopper 22, forming a columnar sample chamber designated generally at 50 and comprised of segments 50a, 50b and 50c.

The discs 14, 16, 18 and 20 are each formed with an arcuate shaped aperture.

The apertures of the discs 14, 16 and 20 are respectively identified as 52, 54 and 58.

The apertures of the discs 14, 16 and 18 have flanges for receiving and supporting sample jars 60. Adapters 62 (FIG. 4) are threaded on the jars 60 and rest on these flanges flush with the top surfaces of the discs as shown for the discs 14 and 16 in FIG. 2 (the uppermost jar in this figure being shown out of position for purposes of illustration). The jars of all discs are vertically aligned when the segments 50a, 50b and 50c are also aligned as shown in FIG. 1.

The bottom disc 14 and the intermediate discs 16 and 18 are each provided with a pin 64 that projects upwardly into an arcuate peripheral groove 66 in the adjacent disc. The cooperation of these pins and grooves facilitates the sequential collection of samples as hereinafter described.

The shaft 26 has a section 26a of reduced cross section as shown in FIG. 1. The disc 20 has a horizontal thru bore into which a pin 68 is inserted in position to bear slidably on the section 26(a). By rotation of the thumb wheel 40 the shaft may be caused to bear downwardly on the pin and on the stack of discs, causing them to be compressed against the cover plate 32 of the base. The compressive force may be released or varied according to the requirements of the test procedure.

A laterally extending threaded bore 70 in the disc 14 communicates with the bore 44, and the latter also receives an assembly comprising a porous membrane 72, a membrane retaining ring 74 and a compression spring 76 formed of a wave spring 76. The bore 70 is adapted for connection to an external source of air or other gas under pressure (not shown). The membrane 72 acts as a diffuser providing a uniform stream of the gas into the test chamber 48.

In use, the test apparatus 10 is initially placed in the position shown in FIGS. 1 and 2 with three empty sample jars 60 in place in the apertures 52, 54 and 56 of the discs. A measured quantity of sample solids with uniform particle size distribution is poured into the funnel 22 and fills the sample chamber 50.

Air or other gas under pressure is then admitted through the bore 70 and through the membrane 72 into the test chamber. The pressure of the gas and the duration of flow is precisely controlled, causing fluidization of the material. The fluidized material expands upwardly because of the presence of gas therein and rises into the hopper 22.

After the gas flow is terminated material in the sample chamber 50 is allowed to remain at rest and deaerate. Then, the discs 20, 18 and 16 are sequentially rotated to deposit the material in the segments 50a, 50b and 50c of the column 50 respectively into the sample jars 60. First, the disc 20 is rotated 90° between the limits of the arcuate groove 66 therein by engagement with the pin 64 projecting from the disc 18, filling the sample jar located in the latter disc. Continued rotation in the same direction through another 90° causes rotation of both of the discs 18 and 20, resulting in the deposit of the material in the segment 50b in the sample jar located in the disc 16, between the limits defined by the groove 66 in the disc 18. Further rotation through another 90° causes all of the discs 16, 18 and 20 to rotate together, resulting in the deposit of the material in the segment 50c in the sample jar located in the disc 14.

The samples in the three jars 60 are then measured or tested by any known assay method, screening method or other test procedure to evaluate the differences in the particle size or chemical concentrations of the material in the respective samples.

What is claimed is:

1. A fluidization segregation tester for bulk particular solids having, in combination, a base supporting a vertically extending shaft, a plurality of discs rotatable about the axis of the shaft and including an uppermost disc and a second disc stacked vertically on the base, each disc having a vertically extending bore spaced from said axis, said discs being independently rotatable to align the respective bores therein to form a sample chamber, the second disc having an aperture for supporting a sample jar, an expansion receptacle connected to the top of the chamber and adapted for filling the chamber with a sample of the solids, and means for connecting the bottom of the chamber to a source of gas under pressure, whereby the sample is fluidized and segregated and expands into said receptacle, the uppermost disc being rotatable to align the bore of the uppermost disc with the aperture in the second disc, whereby the sample jar collects the portion of the fluidized sample within the bore of the uppermost disc.

2. The tester of claim 1, in which the shaft is vertically engageable with the uppermost disc and the base includes means to apply axial tension to the shaft to compress the stack of discs.

3. The tester of claim 2, in which the axial tension means is adapted to apply variable tension to the shaft.

4. The tester of claim 2, in which the shaft has a portion of reduced diameter, and including a pin extending horizontally through the uppermost disc and adjacent to said portion of reduced diameter for vertically engaging the shaft.

5. The tester of claim 1, wherein at least one of the discs is formed with an arcuate groove and an adjacent disc has a projection extending into said groove, whereby the angular displacement between the at least one and adjacent discs is limited to the angle subtended by said groove.

6. A tester according to claim 1, including
a third disc stacked vertically below the second disc and having an aperture for a second sample jar, the uppermost and second discs being rotatable to align the bore of the second disc with the aperture in the third disc, whereby the second sample jar collects the portion of the fluidized sample within the bore of the second disc.

7. A tester according to claim 6, in which the third disc has a vertically extending bore spaced from said axis and is independently rotatable to align the bore of the third disc with the sample chamber.

8. A tester according to claim 7, including
a fourth disc stacked vertically below the third disc and having an aperture for a third sample jar, the uppermost, second and third discs being rotatable to align the bore of the third disc with the aperture in the fourth disc, whereby the third sample jar collects the portion of the fluidized sample within the bore of the third disc.

* * * * *